United States Patent
Tiao et al.

(10) Patent No.: US 11,752,360 B2
(45) Date of Patent: Sep. 12, 2023

(54) MINIMALLY INVASIVE NEUTRON BEAM GENERATING DEVICE AND MINIMALLY INVASIVE NEUTRON CAPTURE THERAPY SYSTEM

(71) Applicant: Heron Neutron Medical Corp., Hsinchu (TW)

(72) Inventors: Kuo Tung Tiao, Hsinchu (TW); Jyi Tyan Yeh, Hsinchu (TW); Zhen Fan You, Hsinchu (TW)

(73) Assignee: HERON NEUTRON MEDICAL CORP., Hsinchu (TW)

( * ) Notice: Subject to any disclaimer, the term of this patent is extended or adjusted under 35 U.S.C. 154(b) by 690 days.

(21) Appl. No.: 16/848,391

(22) Filed: Apr. 14, 2020

(65) Prior Publication Data

US 2021/0322786 A1    Oct. 21, 2021

Related U.S. Application Data

(60) Provisional application No. 62/833,948, filed on Apr. 15, 2019.

(51) Int. Cl.
*A61N 5/10* (2006.01)
*A61B 1/00* (2006.01)
(Continued)

(52) U.S. Cl.
CPC ........ *A61N 5/1014* (2013.01); *A61B 1/00087* (2013.01); *A61B 1/3132* (2013.01);
(Continued)

(58) Field of Classification Search
CPC .... A61N 2005/1018; A61N 2005/1022; A61N 2005/109; A61N 5/1001; A61N 5/1014;
(Continued)

(56) References Cited

U.S. PATENT DOCUMENTS

| 5,547,454 A | 8/1996 | Horn et al. |
| 5,630,786 A | 5/1997 | Griffin et al. |

(Continued)

FOREIGN PATENT DOCUMENTS

| CN | 109420261 A | 3/2019 |
| JP | 11-57043 A | 3/1999 |

(Continued)

OTHER PUBLICATIONS

English translation of JP2014-115122 (Year: 2014).*
(Continued)

*Primary Examiner* — Christine H Matthews
(74) *Attorney, Agent, or Firm* — Birch, Stewart, Kolasch & Birch, LLP (57) ABSTRACT

A minimally invasive neutron beam generating device is provided. The minimally invasive neutron beam generating device includes a proton accelerator, a target, and a neutron moderator. The proton accelerator is connected to a first channel, the target is located at one end of the first channel, and the neutron moderator covers the end of the first channel so that the target is embedded in the neutron moderator. In addition, the neutron moderator includes an accommodating element for accommodating a moderating substance, and the accommodating element is retractable.

20 Claims, 3 Drawing Sheets

(51) Int. Cl.
    *A61B 1/313*     (2006.01)
    *G21K 1/00*     (2006.01)
    *H05H 3/06*     (2006.01)
    *A61B 17/00*     (2006.01)

(52) U.S. Cl.
    CPC ............... *G21K 1/00* (2013.01); *H05H 3/06* (2013.01); *A61B 17/00234* (2013.01); *A61N 2005/109* (2013.01); *A61N 2005/1018* (2013.01); *A61N 2005/1095* (2013.01)

(58) Field of Classification Search
    CPC ......... A61N 5/1077; A61N 2005/1096; H05H 2277/11; H05H 3/06
    See application file for complete search history.

(56) References Cited

U.S. PATENT DOCUMENTS

| | | |
|---|---|---|
| 6,352,500 B1 | 3/2002 | Halpern |
| 6,685,619 B2 | 2/2004 | Halpern et al. |
| 2004/0151368 A1 | 8/2004 | Cruickshank et al. |
| 2010/0067640 A1 | 3/2010 | Willis et al. |
| 2010/0195781 A1 | 8/2010 | Paul et al. |
| 2012/0080618 A1 | 4/2012 | Clayton et al. |
| 2018/0141869 A1 | 5/2018 | Furuya et al. |
| 2018/0177788 A1* | 6/2018 | Pachter .............. A61K 39/3955 |
| 2018/0250528 A1 | 9/2018 | Liu et al. |

FOREIGN PATENT DOCUMENTS

| | | |
|---|---|---|
| JP | 2014-113215 A | 6/2014 |
| JP | 2014-115122 A | 6/2014 |
| JP | 2016-143543 A | 8/2016 |
| JP | 2018-535717 A | 12/2018 |
| TW | 201620577 A | 6/2016 |
| TW | 201912199 A | 4/2019 |

OTHER PUBLICATIONS

Chinese Office Action and Search Report for Chinese Application No. 202010285684.X, dated Mar. 30, 2022.
Japanese Office Action for Japanese Application No. 2020-072763, dated Feb. 24, 2021, with English translation.
Brandão et al., "Intracavitary moderator balloon combined with 252Cf brachytherapy and boron neutron capture therapy, improving dosimetry in brain tumour and infiltrations", Br J Radiol, 2015, 88:20140829, total 11 pages.
Song et al., "Accelerator-based neutron brachytherapy", Med. Phys., vol. 29, No. 1, Jan. 2002, pp. 15-25.
Extended European Search Report for European Application No. 20169248.0, dated Jun. 26, 2020.
Horn et al., "Micro-radiosurgery: a new concept for radiotherapy based upon low energy, ion-induced nuclear reactions," Nuclear Instruments and Methods in Physics Research B79, 1993, XP000353944, pp. 901-906 (6 pages total).
Taiwanese Office Action and Search Report dated May 21, 2021 for Application No. 109111480.

* cited by examiner

MINIMALLY INVASIVE NEUTRON BEAM GENERATING DEVICE AND MINIMALLY INVASIVE NEUTRON CAPTURE THERAPY SYSTEM

CROSS REFERENCE TO RELATED APPLICATIONS

This application claims benefit of U.S. Provisional Application No. 62/833,948, filed on Apr. 15, 2019, the entirety of which is incorporated by reference herein.

BACKGROUND OF THE INVENTION

Field of the Invention

The present disclosure relates to a minimally invasive neutron beam generating device and a minimally invasive neutron capture therapy system.

Description of the Related Art

The principle of boron neutron capture therapy (BNCT) is as follows: boron-containing drugs are combined with tumor cells via blood circulation, and then a neutron beam is emitted at the position of the tumor center, so that the boron may absorb thermal neutrons and generate lithium ions and helium ions, and thus cancer cells are destroyed without destroying adjacent tissues.

At present, most of the BNCT neutron beam source generators are derived from research reactors and accelerators. The neutron beam source generator is generally fixed on the wall and irradiates the neutron from the outside of the patient. Due to the physical characteristics of neutrons, after they enter the human body, they decelerate rapidly and cannot reach deeper positions. Therefore, only the shallow tumors can be treated, and the treatment depth is limited. For example, even through the use of higher-energy epithermal neutron beams, the depth of treatment still cannot be greater than 10 cm.

As described above, although the existing neutron beam generating devices applied to BNCT have been adequate for their intended use, they have not been entirely satisfactory in all respects. Therefore, the development of a neutron beam generating device that can further improve the neutron utilization rate and treatment depth is still one of the topics that the industry is devoted to research.

BRIEF SUMMARY OF THE INVENTION

In accordance with some embodiments of the present disclosure, a minimally invasive neutron beam generating device is provided. The minimally invasive neutron beam generating device includes a proton accelerator, a target, and a neutron moderator. The proton accelerator is connected to a first channel, the target is located at one end of the first channel, and the neutron moderator covers the end of the first channel so that the target is embedded in the neutron moderator. In addition, the neutron moderator includes an accommodating element for accommodating a moderating substance, and the accommodating element is retractable.

In accordance with some embodiments of the present disclosure, a minimally invasive neutron capture therapy system is provided. The minimally invasive neutron capture therapy system includes a neutron beam generating device and an endoscope device adjacent to the neutron beam generating device. The neutron beam generating device includes a proton accelerator, a target, and a neutron moderator. The proton accelerator is connected to a first channel, the target is located at one end of the first channel, and the neutron moderator covers the end of the first channel so that the target is embedded in the neutron moderator. In addition, the neutron moderator includes an accommodating element for accommodating a moderating substance, and the accommodating element is retractable.

A detailed description is given in the following embodiments with reference to the accompanying drawings.

BRIEF DESCRIPTION OF THE DRAWINGS

The disclosure may be more fully understood by reading the subsequent detailed description and examples with references made to the accompanying drawings, wherein.

DETAILED DESCRIPTION OF THE INVENTION

The minimally invasive neutron beam generating device and the minimally invasive neutron capture therapy system provided in the embodiments of the present disclosure are described in detail in the following description. It should be understood that the following description provides many different embodiments or examples for implementing different aspects of some embodiments of the present disclosure. The specific elements and configurations described in the following detailed description are set forth in order to clearly describe the present disclosure. It will be apparent that the exemplary embodiments set forth herein are used merely for the purpose of illustration. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments.

The descriptions of the exemplary embodiments are intended to be read in connection with the accompanying drawings, which are to be considered part of the entire written description. It should be understood that the drawings are not drawn to scale. In fact, the size of the element may be arbitrarily enlarged or reduced in order to clearly express the features of the present disclosure.

In addition, it should be understood that, although the terms "first", "second", "third" etc. may be used herein to describe various elements, components, or portions, these elements, components, or portions should not be limited by these terms. These terms are only used to distinguish one element, component, or portion from another element, component, or portion. Thus, a first element, component, or portion discussed below could be termed a second element, component, or portion without departing from the teachings of the present disclosure.

The terms "about" and "substantially" typically mean+/−10% of the stated value, more typically +/−5% of the stated value, more typically +/−3% of the stated value, more typically +/−2% of the stated value, more typically +/−1% of the stated value and even more typically +/−0.5% of the stated value. The stated value of the present disclosure is an approximate value. When there is no specific description, the stated value includes the meaning of "about" or "substantially". Furthermore, the phrase "in a range between a first value and a second value" or "in a range from a first value to a second value" indicates that the range includes the first value, the second value, and other values between them.

Unless defined otherwise, all technical and scientific terms used herein have the same meaning as commonly understood by one of ordinary skill in the art to which this disclosure belongs. It should be appreciated that, in each case, the term, which is defined in a commonly used dictionary, should be interpreted as having a meaning that conforms to the relative skills of the present disclosure and the background or the context of the present disclosure, and should not be interpreted in an idealized or overly formal manner unless so defined.

Figure 1:
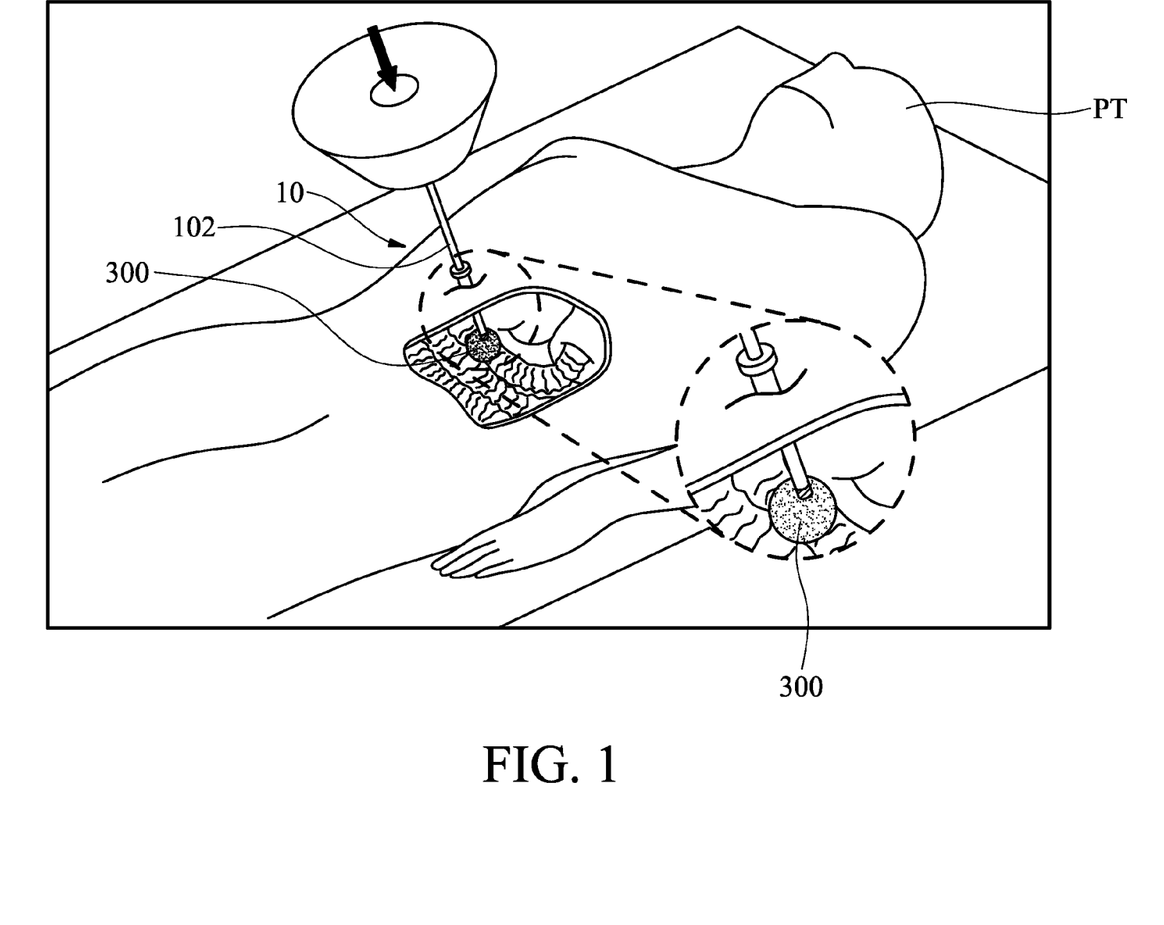
FIG. 1 is a schematic diagram of the use of a minimally invasive neutron beam generating device in accordance with some embodiments of the present disclosure.

Refer to FIG. 1, which is a schematic diagram of the use of a minimally invasive neutron beam generating device 10 in accordance with some embodiments of the present disclosure. As shown in FIG. 1, the minimally invasive neutron beam generating device 10 can be placed in a patient PT for treatment. In other words, the position where the neutron beam is generated (neutron source) can be moved into the body of the patient PT, and the neutron beam can irradiate the tumor nearby. Compared with a general neutron beam generating device that is irradiated outside the body, the minimally invasive neutron beam generating device 10 can improve the use efficiency of the neutron beam, and can be irradiated to a deeper place or the tumor that is shielded by other organs and is less likely to be reached. The effectiveness of BNCT treatment is therefore improved. Furthermore, since the neutron source is close to the tumor, the neutron intensity and energy that are required become lower, and the proton accelerator with low current and low energy can be used, thereby also reducing the need for radiation protection in hospitals.

Figure 2:
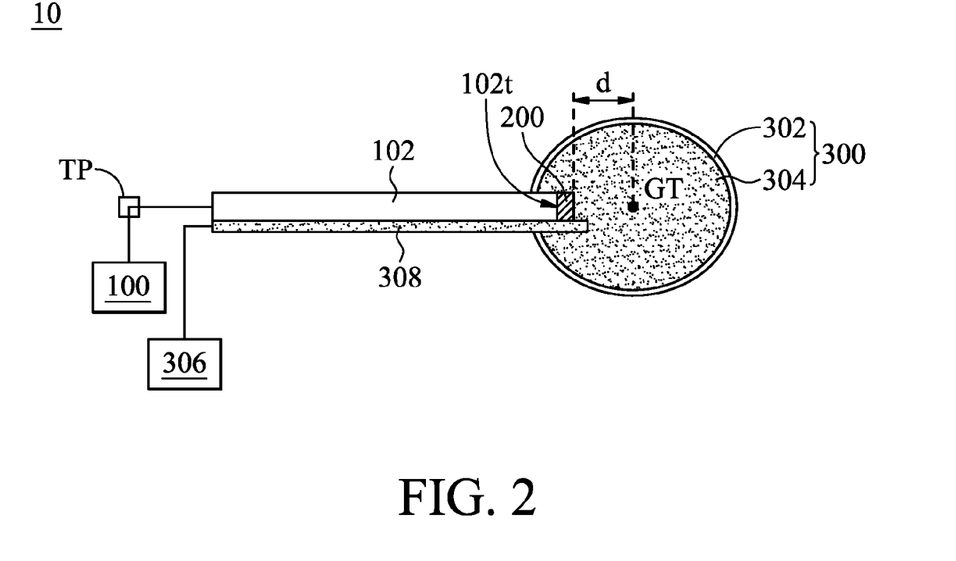
FIG. 2 is a schematic structural diagram of a minimally invasive neutron beam generating device in accordance with some embodiments of the present disclosure.

The detailed structure of the minimally invasive neutron beam generating device 10 is further described as follows. FIG. 2 is a schematic structural diagram of the minimally invasive neutron beam generating device 10 in accordance with some embodiments of the present disclosure. In accordance with some embodiments, additional features may be added to the minimally invasive neutron beam generating device 10 described below.

As shown in FIG. 2, in accordance with some embodiments, the minimally invasive neutron beam generating device 10 may include a proton accelerator 100, a target 200, and a neutron moderator 300. In some embodiments, the proton accelerator 100 may be connected to a first channel 102, and the target 200 may be disposed at the other end of the first channel 102. In some embodiments, the target 200 may be located at an end 102t of the first channel 102. In addition, the neutron moderator 300 may cover the end 102t of the first channel 102 so that the target 200 may be embedded in the neutron moderator 300.

Specifically, the proton accelerator 100 can provide protons of a certain energy. The protons of a certain energy can pass through the first channel 102, and hit the target 200 at the end 102t to generate fast neutrons, and then the neutron moderator 300 can convert neutrons into thermal neutrons to treat the affected part. In some embodiments, the interior of the first channel 102 may be in a vacuum state.

In some embodiments, the target 200 may be located in the first channel 102, or may be located outside the first channel 102 but connected to and in contact with the first channel 102. In addition, in some embodiments, the neutron moderator 300 may cover a portion of the first channel 102, and the neutron moderator 300 may completely cover the target 200, so that the whole target 200 may be located in the neutron moderator 300. In addition, in some embodiments, the first channel 102, the target 200, and the neutron moderator 300 may be a handheld structure.

In some embodiments, the proton accelerator 100 can generate a proton beam with energy in a range from about 2 MeV to about 2.6 MeV. In some embodiments, the proton accelerator 100 may use a current in a range from about 0.1 milliamperes (mA) to about 5 mA.

It should be noted that in accordance with some embodiments of the present disclosure, since the minimally invasive neutron beam generating device 10 can be used directly adjacent to the affected part (e.g., the position of tumor), the energy required for the proton accelerator 100 (e.g., the intensity of current) can be greatly reduced, compared with the proton accelerator that is used in general BNCT. For example, when the proton accelerator used in current BNCT provides a proton beam of about 3 MeV, the current that is used is more than 10 mA, and the treatment time of BNCT is about 30 to 60 minutes. In contrast, in accordance with some embodiments of the present disclosure, when the proton accelerator 100 of the minimally invasive neutron beam generating device 10 provides a proton beam of about 2 MeV to about 3 MeV, the current of only less than 2 mA is required to provide the neutron beam intensity for BNCT treatment for less than 10 minutes.

In some embodiments, the material of the target 200 may include lithium (Li), beryllium (Be), or other suitable materials, but the present disclosure is not limited thereto.

Furthermore, it should be understood that although not shown in the drawings, in accordance with some embodiments, the proton beam generated by the proton accelerator 100 may be focused by a quadrupole magnet first, and then adjusted by the components such as a collimator, a turning magnet etc., and then hit the target 200.

In addition, as shown in FIG. 2, the neutron moderator 300 may include an accommodating element 302, and the accommodating element 302 may be used to accommodate a moderating substance 304. In some embodiments, the minimally invasive neutron beam generating device 10 may further include a moderating substance provider 306, and the moderating substance provider 306 may be used to provide the moderating substance 304. Specifically, the moderating substance provider 306 may be connected to a second channel 308, and the moderating substance provider 306 may deliver the moderating substance 304 to the accommodating element 302 through the second channel 308. In addition, in some embodiments, the first channel 102 that is connected to the proton accelerator 100 and the second channel 308 that is connected to the neutron moderator 300 may be adjacent to or in contact with each other. For example, the first channel 102 and the second channel 308 may be integrated, but the present disclosure is not limited thereto.

Furthermore, in some embodiments, the second channel 308 may also be a handheld structure.

In some embodiments, the accommodating element 302 of the neutron moderator 300 is retractable. In some embodiments, the accommodating element 302 may be formed of a material having a retractable feature, for example, a thermoplastic material. Specifically, in some embodiments, the material of the accommodating element 302 may include rubber, silicone, thermoplastic polyurethane (TPU), polyimide (PI), polycarbonate (PC), polyethylene terephthalate (PET), other suitable materials, or a combination thereof, but the present disclosure is not limited thereto.

In some embodiments, the moderating substance 304 in the neutron moderator 300 may be a hydrogen-containing material. For example, in some embodiments, the moderating substance 304 may include water, heavy water, or other suitable materials, but the present disclosure is not limited thereto. In accordance with the embodiments of the present disclosure, any substance that can effectively reduce the velocity of the neutron beam can be used as the moderating substance 304.

In some embodiments, the neutron moderator 300 may convert high-energy fast neutrons to low-energy thermal neutrons for BNCT treatment. Specifically, in some embodiments, the neutron moderator 300 may reduce the energy range of neutrons to about less than 10 keV. In some embodiments, the neutron moderator 300 may be able to be placed in a body of a patient and directly contact the affected part (e.g., tumor), as shown in FIG. 1.

As described above, in accordance with some embodiments of the present disclosure, since the accommodating element 302 is retractable, the moderating substance 304 may not be filled or only a small amount of moderating substance 304 is filled in the accommodating element 302 before the minimally invasive neutron beam generating device 10 is placed into the patient's PT body, and more moderating substance 304 is further filled into the accommodating element 302 after the minimally invasive neutron beam generating device 10 is placed into patient's PT body so as to effectively decelerate fast neutrons to thermal neutrons. In this way, there is no need to form a large surgical wound on the patient PT, and effective BNCT treatment can be performed in a minimally invasive manner.

As shown in FIG. 2, in some embodiments, after being filled with the moderating substance 304, the accommodating element 302 may have an ellipsoid shape. In some other embodiments, after being filled with the moderating substance 304, the accommodating element 302 may have a spherical shape, an egg shape, an irregular shape, or other suitable shapes. In some embodiments, the accommodating element 302 may have a conformal shape conforming to the environment in the body. It should be understood that the accommodating element 302 may have any suitable shape, and is not limited to those shown in the drawings. In various embodiments, the accommodating element 302 may be adjusted to have an appropriate shape according to actual needs and medical plans.

In addition, in some embodiments, after the moderating substance 304 is filled in the accommodating element 302, the target 200 does not overlap the geometric center (not labeled in the drawing) of the neutron moderator 300. That is, the target 200 may deviate from the geometric center of the neutron moderator 300. Specifically, in some embodiments, a distance d between the target 200 and a geometric center GT of the neutron moderator 300 may be in a range from about 0 cm to about 2 cm. If the distance d is too small, the neutron moderator needs to be enlarged to have enough moderating substance to decelerate fast neutrons to thermal neutrons. If the distance d is too large, there needs to be a sufficient size of neutron moderator accordingly. Therefore, whether the distance d is too small or too large, the size of the neutron moderator will be too large, and thus the neutron moderator is not suitable to be placed in the body of the patient PT. In accordance with some embodiments, the distance d refers to the minimum distance between the target 200 and the geometric center GT of the neutron moderator 300 in an extending direction of the first channel 102.

Moreover, in some embodiments, after the moderating substance 304 is filled in the accommodating element 302, the diameter of the neutron moderator 300 may be in a range from about 3 cm to about 12 cm, but the present disclosure is not limited thereto. In accordance with some embodiments, the diameter of the neutron moderator 300 refers to the largest diameter of the accommodating element 302 after filling with the moderating substance 304. In addition, it should be understood that in various embodiments, the diameter (or size) range of the neutron moderator 300 may be adjusted according to the energy of the proton accelerator 100 to achieve the desired therapeutic effect.

As shown in FIG. 2, in some embodiments, the minimally invasive neutron beam generating device 10 may further include a rotating joint TP, and the rotating joint TP may be located between the proton accelerator 100 and the first channel 102. In particular, the position of the proton accelerator 100 generally cannot be moved arbitrarily, but the rotating joint TP makes the operation position of the minimally invasive neutron beam generating device 10 more flexible, facilitates tumor localization, and penetrates into the body in a specific direction for treatment.

Figure 3:
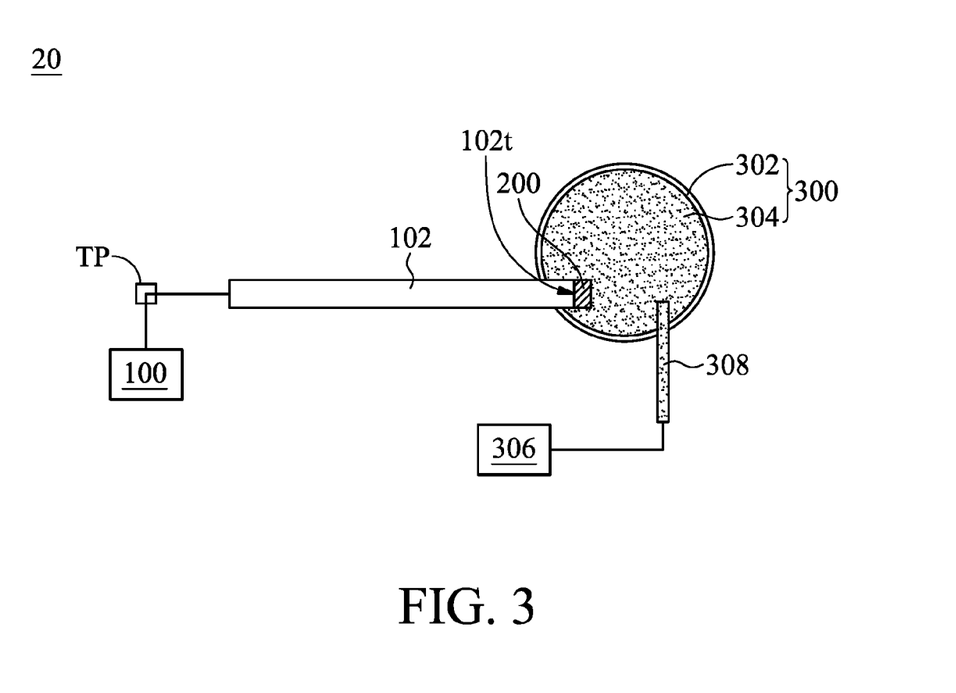
FIG. 3 is a schematic structural diagram of a minimally invasive neutron beam generating device in accordance with some embodiments of the present disclosure.

Next, refer to FIG. 3, which is a schematic structural diagram of a minimally invasive neutron beam generating device 20 in accordance with some other embodiments of the present disclosure. It should be understood that the same or similar components or elements in above and below contexts are represented by the same or similar reference numerals. The materials, manufacturing methods and functions of these components or elements are the same or similar to those described above, and thus will not be repeated herein.

As shown in FIG. 3, in some embodiments, the first channel 102 that is connected to the proton accelerator 100 and the second channel 308 that is connected to the neutron moderator 300 may be separately disposed. In some embodiments, the proton accelerator 100 and the neutron moderator 300 may be operated independently. Similarly, in this embodiment, the neutron moderator 300 may cover the end 102t of the first channel 102 so that the target 200 is embedded in the neutron moderator 300. Furthermore, as shown in FIG. 3, in some embodiments, after being filled with the moderating substance 304, the accommodating element 302 may have a spherical shape.

Figure 4:
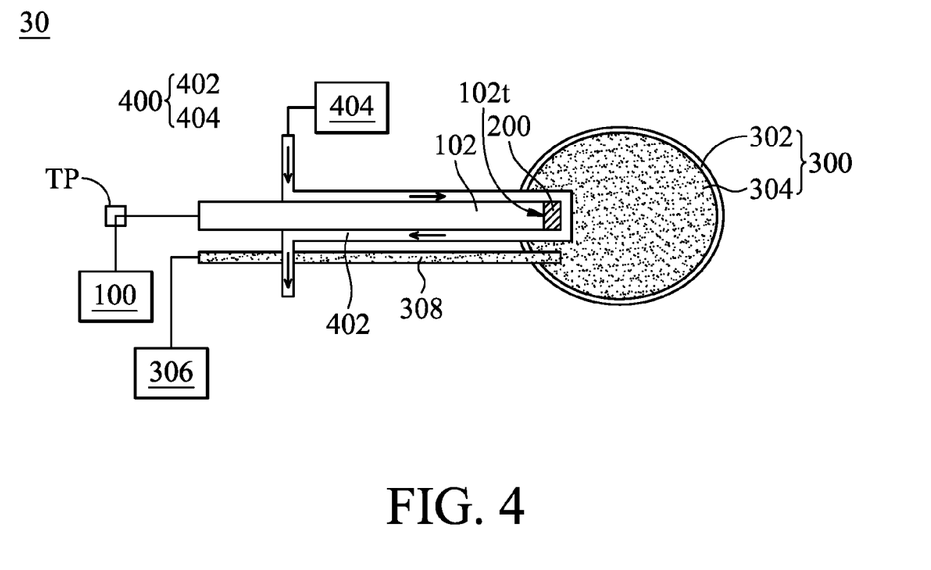
FIG. 4 is a schematic structural diagram of a minimally invasive neutron beam generating device in accordance with some embodiments of the present disclosure.

Next, refer to FIG. 4, which is a schematic structural diagram of a minimally invasive neutron beam generating device 30 in accordance with some other embodiments of the present disclosure. As shown in FIG. 4, in accordance with some embodiments, the minimally invasive neutron beam generating device 30 may further include a cooling element 400, and the cooling element 400 may be adjacent to the first channel 102 and surround the target 200.

Specifically, in some embodiments, the cooling element 400 may include a third channel 402 and a cooling source provider 404 that is connected to the third channel 402. The cooling source provider 404 may provide a cooling source such as cooling water, and the third channel 402 may be used to transport or circulate the cooling source. In some embodiments, the third channel 402 may surround most of the first channel 102 and contact the first channel 102 and the target 200. In some embodiments, the third channel 402 also contacts the neutron moderator 300. In some embodiments, the cooling source may be circulated in the third channel 402, and the cooling source may take the heat generated during the process where the protons hit the target 200 to generate neutrons away.

Furthermore, as shown in FIG. 4, in some embodiments, the first channel 102 that is connected to the proton accelerator 100 and the second channel 308 that is connected to the neutron moderator 300 may be adjacent to each other but separately disposed. In addition, in some embodiments, the third channel 402 for delivering the cooling source and the second channel 308 for delivering the moderating substance 304 may also be adjacent to or in contact with each other. For example, the third channel 402 and the second channel 308 may be integrated, but the present disclosure is not limited thereto.

In some other embodiments, the moderating substance 304 may be the same as the cooling source, and therefore the moderating substance provider 306 and the cooling source provider 404 may be disposed alternatively and simultaneously connected to the second channel 308 and the third channel 402. In still some other embodiments, the second channel 308 loaded with the moderating substance 304 may have a cooling function itself, so no additional cooling element 400 is required.

Figure 5:
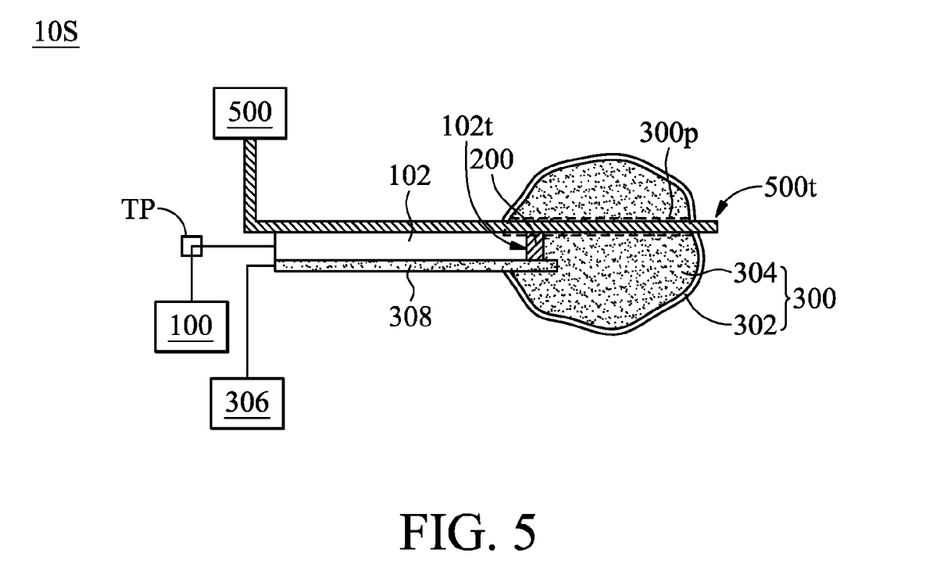
FIG. 5 is a schematic structural diagram of a minimally invasive neutron capture therapy system in accordance with some embodiments of the present disclosure.

Next, refer to FIG. 5, which is a schematic structural diagram of a minimally invasive neutron capture therapy system 10S in accordance with some embodiments of the present disclosure. In accordance with some embodiments, the minimally invasive neutron capture therapy system 10S may include the minimally invasive neutron beam generating device 10 (not labeled in the drawing) as described above and an endoscope device 500, and the endoscope device 500 may be adjacent to the minimally invasive neutron beam generating device 10. The configuration of the minimally invasive neutron beam generating device 10 is as described above, and thus will not be repeated herein. In such a configuration, the real-time image of the patient PT can be obtained, the position of the relevant organ or tumor can be identified in real time, and accordingly a correct dose of neutron irradiation can be provided accurately.

As shown in FIG. 5, in some embodiments, the endoscope device 500 may penetrate the neutron moderator 300 so that an end 500t of the endoscope device 500 may be located outside the neutron moderator 300, thereby the images in front of the neutron moderator 300 can be observed. In addition, in some embodiments, the neutron moderator 300 may have a hole 300p, and the endoscope device 500 may be located in the hole 300p and penetrate the hole 300p. Specifically, in some embodiments, the hole 300p may be located within the accommodating element 302.

As shown in FIG. 5, in some embodiments, the endoscope device 500 and the first channel 102 of the minimally invasive neutron beam generating device 10 may be adjacent to or in contact with each other. For example, the endoscope device 500 and the first channel 102 may be integrated, but the present disclosure is not limited thereto. It is worth noting that this configuration is particularly suitable for surgical applications, e.g., the surgery in esophageal cancer, colorectal cancer, or rectal cancer and so on.

Furthermore, although not shown in the drawings, in some other embodiments, the endoscope device 500 and the minimally invasive neutron beam generating device 10 may be separately disposed.

To summarize the above, in accordance with some embodiments of the present disclosure, the minimally invasive neutron beam generating device is provided. With such a device, the position for generating neutron beam (neutron source) can be placed in the patient's body, and the neutron beam can irradiate the tumor nearby. Therefore, the minimally invasive neutron beam generating device can improve the use efficiency of the neutron beam, can also reduce the risk of damage to other healthy cells. In addition, the neutron beam can be irradiated to a deeper place or a tumor that is shielded by other organs and is less likely to be reached. The effectiveness of BNCT treatment is therefore improved. Furthermore, since the neutron source is close to the tumor, the neutron intensity and energy that are required can be reduced. The proton accelerator with low energy can be used, thereby also reducing the need for radiation protection in the hospitals.

In addition, it should be understood that in accordance with some embodiments, the aforementioned minimally invasive neutron beam generating device may further include other auxiliary elements that are known in the art, and these elements may be present in any form or configuration known to those with ordinary skill in the art.

A detailed description is given in the following particular embodiments in order to provide a thorough understanding of the above and other objects, features and advantages of the present disclosure. However, the scope of the present disclosure is not intended to be limited to the particular embodiments.

Examples 1 to 14

Geometric Model Analysis

The following analysis was conducted by simulation calculation software MCNP6, which was developed by Los Alamos National Laboratory, and the cross-section library ENDF/B-7 was used.

In Examples 1 to 14, a brain phantom with a size of 18 cm×18 cm×20 cm was used for the simulation test. The brain phantom was composed of elements reported by ICRU46. In the neutron beam generating device that was used, the diameter of the proton beam channel (the first channel) was 3 millimeters (mm) and the length was from the surface of the brain phantom to the target, and water was used as the moderating substance. Furthermore, a lithium target with a thickness of 0.1 mm and a diameter of 1 cm was used as the target, and the lithium target deviated from the center of the neutron moderator.

Dose Assessment Indexes in Phantom

The dose of the brain phantom was evaluated, and the assessment indexes were the therapeutic ratio (TR) and the treatment time.

BNCT treatment was performed on the brain phantom, and its physical therapeutic dose was derived from neutron dose, photon dose and boron dose. The weighted therapeutic doses were as follow: the neutron dose multiplied by Relative Biological Effective (RBE), the photon dose multiplied by RBE, and the boron dose multiplied by Compound Biological Effective (CBE). The RBE of the neutron was 3.2, the RBE of the photon was 1, the CBE of the brain phantom was 1.3, and the CBE of the tumor was 3.8. The RBE and CBE were referred to M. S. Herrera et al. "Treatment planning capability assessment of a beam shaping assembly for accelerator-based BNCT", Applied Radiation and Isotopes 69 (2011) 1870-1873.

Specifically, the therapeutic ratio (TR) was defined as the ratio of the total weighted therapeutic dose of tumor to the maximum total weighted dose of normal tissue at any point in the phantom. This value represents the treatment quality to the tumor at that position. The larger the TR, the better the treatment quality to the tumor at that position. The maximum TR value represents the best effect of the treatment. If the normal tissue at any position of the phantom reaches the weighted dose of 10 Gy, the time that is required to reach such a dose is the treatment time.

Calculation of Assessment Indexes

Assuming that the boron concentration in normal tissue was 25 ppm, the concentration ratio of boron in tumor tissue to normal tissue (T/N ratio) was 3, the count (Tally) was performed using the central axis as a center, and the cross section is 2 cm×2 cm (behind the moderator). The calculation results of BNCT feasibility assessment are shown in Table 1 to Table 6.

TABLE 1

|  | Example 1 | Example 2 | Example 3 |
|---|---|---|---|
| Proton energy (MeV) | 1.9 | 2 | 2.3 |
| Proton current (mA) | 1 | 1 | 1 |
| Maximum diameter of moderator (cm) | 8 | 8 | 8 |
| Maximum TR | 4.81 | 4.32 | 2.68 |
| Treatment time (min) | 72.81 | 9.25 | 1.09 |

According to the results shown in Table 1, the higher the proton energy, the higher the neutron yield and the shorter the treatment time. However, the higher the neutron energy produced after hitting the lithium target, the worse the maximum therapeutic ratio.

TABLE 2

|  | Example 2 | Example 4 | Example 5 | Example 6 |
|---|---|---|---|---|
| Proton energy (MeV) | 2 | 2 | 2 | 2 |
| Proton current (mA) | 1 | 1 | 1 | 1 |
| Maximum diameter of moderator (cm) | 8 | 8 | 8 | 8 |
| Maximum TR | 4.32 | 4.49 | 4.67 | 3.52 |
| Treatment time (min) | 9.25 | 10.37 | 11.44 | 13.44 |
| Deviated distance of lithium target from center of neutron moderator (cm) | 0 | 0.25 | 0.5 | 2 |

According to the results shown in Table 2, the deviated distance (d) of the lithium target from the center of the neutron moderator also affected the maximum value of the therapeutic ratio. When the deviated distance d was within a certain range, the larger the deviated distance d, the larger the maximum value of the therapeutic ratio. However, if the deviated distance d was too large, the total weighted dose of normal tissue on both sides of the channel became larger, and the maximum value of the therapeutic ratio would be decreased. In Example 6, the maximum therapeutic ratio decreased to 3.52, and the treatment time also increased to 13.44 minutes.

TABLE 3

|  | Example 2 | Example 7 |
|---|---|---|
| Proton energy (MeV) | 2 | 2 |
| Proton current (mA) | 1 | 1 |
| Maximum diameter of moderator (cm) | 8 | 5 |
| Maximum TR | 4.32 | 4.05 |
| Treatment time (min) | 9.25 | 8.24 |
| Deviated distance of lithium target from center of neutron moderator (cm) | 0 | 1.25 |

According to the results shown in Table 3, when the lithium target deviated from the neutron moderator by a certain distance and the maximum value of the therapeutic ratio increased, the maximum diameter of the water moderator could be reduced, so that the water moderator entering the human body did not have to occupy too much space.

TABLE 4

|  | Example 3 | Example 8 | Example 9 | Example 10 |
|---|---|---|---|---|
| Proton energy (MeV) | 2.3 | 2.3 | 2.3 | 2.4 |
| Proton current (mA) | 1 | 1 | 1 | 1 |
| Maximum diameter of moderator (cm) | 8 | 11 | 11 | 12 |
| Maximum TR | 2.68 | 3.55 | 4.03 | 3.85 |
| Treatment time (min) | 1.09 | 2.33 | 3.93 | 4.03 |
| Deviated distance of lithium target from center of neutron moderator (cm) | 0 | 0 | 1.25 | 2 |

According to the results shown in Table 4, the larger the maximum diameter of the water moderator, the larger the maximum value of TR. When the maximum diameter of the water moderator was changed from 8 cm (Example 3) to 11 cm (Example 8), the maximum therapeutic ratio was increased to 3.55. Moreover, when the lithium target deviated from the center of the neutron moderator by 1.25 cm, the maximum value of TR was further increased to 4.03. By using similar means, when the incident proton energy of 2.4 MeV was used, the therapeutic ratio was increased to 3.85.

TABLE 5

|  | Example 11 | Example 12 |
|---|---|---|
| Proton energy (MeV) | 2.5 | 2.6 |
| Proton current (mA) | 1 | 1 |
| Maximum diameter of moderator (cm) | 12 | 12 |
| Maximum TR | 3.76 | 3.52 |
| Treatment time (min) | 3.18 | 2.72 |

TABLE 5-continued

|  | Example 11 | Example 12 |
| --- | --- | --- |
| Deviated distance of lithium target from center of neutron moderator (cm) | 2 | 2 |

According to the results shown in Table 5, when the incident proton energy was 2.6 MeV and the maximum diameter of the water moderator was 12 cm, the maximum value of the therapeutic ratio could still reach more than 3.5.

TABLE 6

|  | Example 7 | Example 9 | Example 13 | Example 14 |
| --- | --- | --- | --- | --- |
| Proton energy (MeV) | 2 | 2.3 | 2 | 2.3 |
| Proton current (mA) | 1 | 1 | 0.824 | 0.393 |
| Treatment time (min) | 8.24 | 3.93 | 10 | 10 |

According to the results shown in Table 6, if the treatment time was maintained at 10 minutes, the required accelerator current could be less than 1 mA, which could make the heat dissipation condition of the target design more flexible. Conversely, if there is sufficient ability to dissipate heat, the current can be increased so that the treatment time can be shortened in proportion.

In addition, according to the results shown in Table 1 to Table 6, it can be seen that when the proton energy is within a range of 2.0 MeV to 2.6 MeV, the diameter of the moderator is from 5 cm to 12 cm, and the maximum value of the therapeutic ratio can reach 3.5 or more. From the foregoing simulation calculation results, it can be known that under the conditions used in Table 1 to Table 6, the minimally invasive neutron beam generating device can be effectively applied to BNCT treatment, can treat deep tumors, and the treatment time can be less than 30 minutes. Moreover, compared with the general BNCT treatment that currently exists (providing a proton beam below about 3 MeV and a current greater than 10 mA is required), the provided minimally invasive neutron beam generating device only needs the current of less than 1 mA to provide the proton beam with about 2 MeV to 2.6 MeV of energy, according to the results shown in Table 1 to Table 6.

Although the embodiments and advantages of this disclosure have been disclosed as above, it should be understood that any person with ordinary knowledge in the technical field can make changes, substitutions and substitutions without departing from the spirit and scope of this disclosure. Retouch. In addition, the scope of protection of this disclosure is not limited to the processes, machines, manufacturing, material composition, devices, methods and steps in the specific embodiments described in the description. Any person with ordinary knowledge in the technical field to which this disclosure pertains may disclose content from this disclosure. To understand the current or future development of processes, machines, manufacturing, material composition, devices, methods and steps, as long as they can implement substantially the same functions or achieve approximately the same results in the embodiments described herein, they can be used according to this disclosure. Therefore, the scope of protection of this disclosure includes the aforementioned processes, machines, manufacturing, material composition, devices, methods and steps. In addition, each patent application scope constitutes a separate embodiment, and the protection scope of this disclosure also includes a combination of each patent application scope and embodiment. The scope of protection of this disclosure shall be determined by the scope of the appended patent application.

What is claimed is:

1. A minimally invasive neutron beam generating device, comprising:
    a proton accelerator connected to a first channel;
    a target located at one end of the first channel; and
    a neutron moderator covering the end of the first channel so that the target is embedded in the neutron moderator, wherein the neutron moderator comprises an accommodating element for accommodating a moderating substance, the accommodating element is retractable, and the neutron moderator is able to be placed in a body of a patient.

2. The minimally invasive neutron beam generating device as claimed in claim 1, further comprising a moderating substance provider connected to a second channel, wherein the moderating substance provider delivers the moderating substance into the accommodating element through the second channel.

3. The minimally invasive neutron beam generating device as claimed in claim 1, wherein the moderating substance is a hydrogen-containing substance.

4. The minimally invasive neutron beam generating device as claimed in claim 1, wherein the target does not overlap a geometric center of the neutron moderator.

5. The minimally invasive neutron beam generating device as claimed in claim 1, wherein a diameter of the neutron moderator is in a range from 3 cm to 12 cm.

6. The minimally invasive neutron beam generating device as claimed in claim 1, wherein a material of the target comprises lithium (Li).

7. The minimally invasive neutron beam generating device as claimed in claim 1, wherein the proton accelerator generates a proton beam with energy in a range from 2 MeV to 2.6 MeV.

8. The minimally invasive neutron beam generating device as claimed in claim 1, wherein the proton accelerator uses a current ranging from 0.1 mA to 5 mA.

9. The minimally invasive neutron beam generating device as claimed in claim 1, further comprising a cooling element adjacent to the first channel and surrounding the target.

10. The minimally invasive neutron beam generating device as claimed in claim 1, further comprising a rotating joint located between the proton accelerator and the first channel.

11. The minimally invasive neutron beam generating device as claimed in claim 1, wherein the first channel, the target and the neutron moderator collectively form a hand-held structure.

12. A minimally invasive neutron capture therapy system, comprising:
    a neutron beam generating device, comprising:
        a proton accelerator connected to a first channel;
        a target located at one end of the first channel; and
        a neutron moderator covering the end of the first channel so that the target is embedded in the neutron moderator, wherein the neutron moderator comprises an accommodating element for accommodating a moderating substance, the accommodating element is retractable, and the neutron moderator is able to be placed in a body of a patient; and an endoscope device adjacent to the neutron beam generating device.

13. The minimally invasive neutron capture therapy system as claimed in claim 12, wherein the endoscope device penetrates the neutron moderator.

14. The minimally invasive neutron capture therapy system as claimed in claim 12, wherein the neutron moderator has a hole, and the endoscope device penetrates through the hole.

15. The minimally invasive neutron capture therapy system as claimed in claim 14, wherein the hole is located within the accommodating element.

16. The minimally invasive neutron capture therapy system as claimed in claim 15, wherein the neutron beam generating device further comprises a moderating substance provider connected to a second channel, wherein the moderating substance provider delivers the moderating substance into the accommodating element through the second channel.

17. The minimally invasive neutron capture therapy system as claimed in claim 12, wherein the target does not overlap with a geometric center of the neutron moderator.

18. The minimally invasive neutron capture therapy system as claimed in claim 12, wherein the proton accelerator generates a proton beam with energy in a range from 2 MeV to 2.6 MeV.

19. The minimally invasive neutron capture therapy system as claimed in claim 12, wherein the proton accelerator uses a current ranging from 0.1 mA to 5 mA.

20. The minimally invasive neutron capture therapy system as claimed in claim 12, wherein the first channel, the target and the neutron moderator collectively form a hand-held structure.

* * * * *